United States Patent
Trouve

(10) Patent No.: US 6,221,919 B1
(45) Date of Patent: Apr. 24, 2001

(54) UTILIZATION OF ETHOXYLATED FATTY ACID ESTERS AS SELF-EMULSIFIABLE COMPOUNDS

(75) Inventor: Gërard Trouve, Castres (FR)

(73) Assignee: SEPPIC, Paris (FR)

( * ) Notice: Subject to any disclaimer, the term of this patent is extended or adjusted under 35 U.S.C. 154(b) by 0 days.

(21) Appl. No.: 09/361,225

(22) Filed: Jul. 27, 1999

Related U.S. Application Data

(63) Continuation of application No. 08/860,468, filed on Jul. 9, 1997, now Pat. No. 6,103,770.

(51) Int. Cl.$^7$ .................................................. C07C 53/00

(52) U.S. Cl. ........................................... 514/786; 554/227

(58) Field of Search ............................. 554/227; 514/786

(56) References Cited

U.S. PATENT DOCUMENTS 5,676,970 * 10/1997 Okuyama et al. .................. 424/449

* cited by examiner

*Primary Examiner*—Deborah D Carr
(74) *Attorney, Agent, or Firm*—Dennison, Scheiner, Schultz & Wakeman

(57) ABSTRACT

The present invention relates to the use of ethoxylated fatty acid esters as self-emulsifiable compounds particularly useful for the preparation of phytosanitary treatment products or as drugs for veterinary or human use. According to the invention, said fatty acid esters comprise a total number of ethylene oxide molecules such that the HLB value (hydrophilic-lipophilic balance) of said compounds is comprised between about 4 and about 10, preferably between about 5 and about 9. Said ethoxylated fatty acid esters form in an original way self-emulsifiable components without requiring any other surfactant, and they are biodegradable and capable of dissolving active principles which are little or non water-soluble.

19 Claims, No Drawings

UTILIZATION OF ETHOXYLATED FATTY ACID ESTERS AS SELF-EMULSIFIABLE COMPOUNDS

This application is a continuation of U.S. application Ser. No. 08/860,468, filed Jul. 9, 1997, now U.S. Pat. No. 6,103,770.

BACKGROUND OF THE INVENTION

The present invention generally relates to the use of ethoxylated fatty acid esters as self-emulsifiable compounds, particularly useful for preparing phytosanitary treatment products or medicines for veterinary or human use.

It is known that an emulsion is a mixture of water and oil stabilised by surfactants.

The dispersion of oil in water (or water in oil) in the form of droplets sufficiently fine for obtaining a stable emulsion necessitates bringing about energy which is often considerable.

Furthermore, any oily preparation is called self-emulsifiable which is capable of forming a stable emulsion with an aqueous phase, practically without bringing about energy, by dispersion in the aqueous phase by slow mechanical stirring for example.

Self-emulsifiable compositions are particularly appreciated each time that mixtures with an aqueous phase, generally water, must be prepared without the need for efficient means of stirring.

Thus, it is notably a matter of:
 within the context of domestic uses, e. g. for the preparation of household cleaning materials or gardening products;
 within the context of agricultural uses, e. g. for the preparation of phytosanitary products intended for storage in tanks or other containers;
 in the pharmaceutical field, e. g. for the preparation of extemporaneously made medicines.

Self-emulsifiable preparations have been described for a long time in the state of the art, especially in the agrochemical field.

These preparations are generally constituted of mineral oils or petroleum fractions to which not very harmful surfactants such as ethoxylated alkyl phenols in particular have been added.

Such preparations are however weakly biodegradable and therefore represent a potential danger to the environment, which has limited the development of them over the last years.

Recently, research has been orientated towards substitute products for petroleum oils and the use has been recommended to this end of biodegradable oils such as triglycerides or methyl esters of fatty acids in particular.

However, these oils are much more difficult to emulsify than mineral oils.

Furthermore, it has also been envisaged to replace ethoxylated alkyl phenols by biodegradable surfactants, but this has proved to be extremely difficult for cost and efficiency reasons.

SUMMARY OF THE INVENTION

Within this context, the aim of the present invention is to solve the technical problem which consists in providing a novel self-emulsifiable composition which is particularly useful for preparing phytosanitary treatment products or medicines for veterinary or human use, whose implementation is easy and which has a sufficient biodegradable character to fulfil the concerns of respect of the environment.

DETAILED DESCRIPTION OF THE INVENTION

It has been discovered, and this constitutes the basis of the present invention, that certain esters obtained by reaction between fatty acids, low molecular weight alcohols or polyols and ethylene oxide constitute self-emulsifiable components without the aid of any other surfactant, and are biodegradable and capable of dissolving active principles which are little or not soluble in water.

Thus, according to a first aspect, the present application aims at covering the use of ethoxylated fatty acid esters having one of the following formulae:

$$R_1-\overset{O}{\underset{\|}{C}}-(O-CH_2-CH_2)_k-OR_2 \quad (I)$$

$$R_3-\overset{O}{\underset{\|}{C}}-(O-CH_2-CH_2)_l-OR_4O-(CH_2-CH_2-O)_m-\overset{O}{\underset{\|}{C}}-R_5 \quad (II)$$

$$R_6-\overset{O}{\underset{\|}{C}}-(O-CH_2-CH_2)_n-O-R_7-\underset{\underset{O-(CH_2-CH_2-O)_p-\overset{\|}{\underset{O}{C}}-R_8}{|}}{CH}-R_9-O-(CH_2-CH_2)_q-O-\overset{O}{\underset{\|}{C}}-R_{10} \quad (III)$$

in which:
 $R_1$, $R_3$, $R_5$, $R_6$, $R_8$ and $R_{10}$ represent a linear or branched, saturated or unsaturated hydrocarbon chain having from 5 to 30 carbon atoms;
 $R_2$, $R_4$, $R_7$ and $R_9$ represent a linear or branched, saturated or unsaturated hydrocarbon chain having from 1 to 5 carbon atoms;
 the total number of ethylene oxide molecules represented in the above-mentioned formulae I, II and III by k, l+m, n+p+q respectively being an integer such that the HLB value (hydrophilic-lipophilic balance) of said compounds be between about 4 and about 10, preferably between about 5 and about 9; and, preferably still, neighbouring 5.
 as self-emulsifiable compounds which are particularly useful for preparing phytosanitary products or medicines for veterinary or human use.

Advantageously, it will be possible for the following products, as well as mixtures thereof, to be used in accordance with the present invention:

Ethoxylated fatty acid esters having the above-mentioned formula I in which $R_1$ is selected from palmitic, stearic, ricinoleic, oleic, linoleic and linolenic acid residues; $R_2$ represents a methyl radical and k is an integer between 1 and 5, preferably equal to 2;

Ethoxylated fatty acid esters having the above-mentioned formula III in which:
$R_6$, $R_8$ and $R_{10}$ represent hydrocarbon chains corresponding to the fatty chains of a vegetable oil;
$R_7$ and $R_9$ represent a methylene group $CH_2$;
n, p, q are integers such that their sum be between 3 and 30.

Ethoxylated fatty acid esters having the above-mentioned formula III in which:
$R_6$, $R_8$ and $R_{10}$ represent hydrocarbon chains having from 16 to 22 carbon atoms corresponding to the fatty chains of rapeseed oil;
$R_7$ and $R_9$ represent a methylene group $CH_2$;
n, p, q are integers such that their sum be between 3 and 30, and preferably equal to 20;

Ethoxylated fatty acid esters having the above-mentioned formula III in which:
$R_6$, $R_8$ and $R_{10}$ represent hydrocarbon chains corresponding to the fatty chains of castor oil;
$R_7$ and $R_9$ represent a methylene radical $CH_2$;
n, p and q represent integers such that their sum be between 5 and 7.

Within the context of the present description and claims, "hydrocarbon chain" is understood as meaning any chain constituted exclusively of carbon atoms and hydrogen atoms.

Alkyls, alkenyl or alkynyl chains constitute examples of such hydrocarbon chains.

The hydrophilic-lipophilic balance (also referred to as HLB) is defined by the following formula:

$$HLB = 20\left(1 - \frac{SI}{AI}\right)$$

in which:
SI represents the saponification index of the product measured according to the NFT 60206 standard; and
AI represents the acid index of the acid used for the manufacture of the product measured according to the NFT 60204 standard.

The most interesting compounds within the context of the present invention are those which are liquid at ambient temperature.

The mixture of several products having the above-mentioned formulae I, II and III may be used advantageously for the preparation of specific self-emulsifiable compositions having particular density, viscosity or coagulation point characteristics.

The addition of biodegradable solvents which are miscible with these products, such as triglycerides, glycols, low molecular weight esters or ketones is also conceivable.

Esters or ketones having known solvent properties and which are generally obtained by condensation of a short-chain fatty acid (less than 10 carbon atoms) with an alcohol of less than 10 carbon atoms are referred to as low molecular weight esters or ketones.

Methyl isobutyl ketone, methyl ethyl ketone, ethyl acetate, amyl acetate, isoamyl acetate are examples thereof.

As examples of a preferred biodegradable solvent, propylene glycol, glycerine and glycerol triacetate can be mentioned.

It will be possible for these solvents to be present in the self-emulsifiable composition in amounts ranging from 0 to about 50% by weight compared to the total weight of the composition.

Ethoxylated fatty acid esters having a chemical structure very close to that of compounds of above-mentioned formulae I, II and III have been described in the literature, e. g. in the U.S. Pat. No. 2,678,935; U.S. Pat. No. 3,539,518; U.S. Pat. No. 4,022,808; GB 1,050,497 documents.

However, the prior documents contain no indication enabling the person skilled in the art to deduce that certain ethoxylated fatty acid esters having above-mentioned formulae I to III would constitute a self-emulsifiable phase.

The compounds used within the context of the present invention can be easily prepared by chemical methods similar to those described in the above-mentioned state of the art.

Generally, these compounds can be obtained:
either by an esterification of ethoxylated alcohols as described in the U.S. Pat. No. 3,539,518 document which is incorporated herein by way of reference;
or, preferably, by ethoxylation of esters having the general formulae:

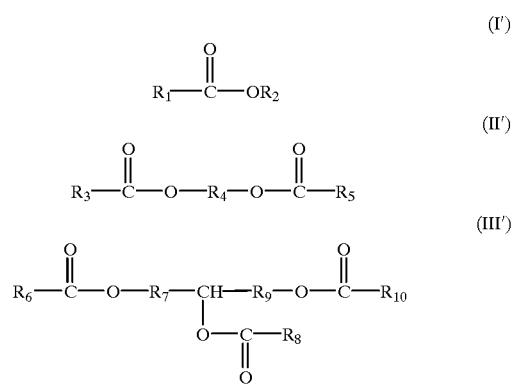

in which,
$R_1$, $R_2$, $R_3$, $R_4$, $R_5$, $R_6$, $R_7$, $R_8$, $R_9$, $R_{10}$ are such as previously defined,
as described in the GB 1,050,497 document which is also incorporated herein by way of reference.

The ethoxylation reaction will generally be carried out by the reaction of ethylene oxide with a previously dried ester in the presence of a basic catalyst, the reaction conditions (amount of ethylene oxide, pressure, temperature and duration) being determined as a function of the total number of ethylene oxide molecules sought after.

According to a second aspect, the present application aims at covering the phytosanitary treatment products as well as the medicines for veterinary or human use which contain a self-emulsifiable composition essentially consisting of at least one compound of formula I, II or III such as defined previously.

According to a particular characteristic, this self-emulsifiable composition can further contain a biodegradable solvent which is miscible with said ethoxylated fatty acid esters, and which is preferably selected from triglycerides, glycols, low molecular weight esters and ketones.

In this case, the biodegradable solvent content within the self-emulsifiable composition will generally be less than or equal to 50% by weight.

Generally, phytosanitary treatment products or pharmaceutical products for veterinary or human use will contain at least one active material or one active principle in association with a self-emulsifiable composition in relative proportions ranging from about 1/99 to 90/10 according to the active principles and the use sought after.

According to a third aspect, the present application aims at covering a method for preparing a phytosanitary treatment product or pharmaceutical product for veterinary or human use in the form of a stable emulsion, characterised in that it consists in mixing, practically without bringing about energy, by dispersion by slow mechanical stirring for example, an aqueous phase and a self-emulsifiable composition having at least one ethoxylated fatty acid ester having one of the following formulae:

$$R_1-\overset{O}{\underset{\|}{C}}-[O-CH_2-CH_2]_k-OR_2 \quad (I)$$

$$R_3-\overset{O}{\underset{\|}{C}}-[O-CH_2-CH_2]_l-OR_4O-[CH_2-CH_2-O]_m-\overset{O}{\underset{\|}{C}}-R_5 \quad (II)$$

$$R_6-\overset{O}{\underset{\|}{C}}-[O-CH_2-CH_2]_n-O-R_7-\underset{\underset{O-[CH_2-CH_2-O]_p-\overset{O}{\underset{\|}{C}}-R_8}{|}}{CH}-R_9-O-[CH_2-CH_2-O]_q-\overset{O}{\underset{\|}{C}}-R_{10} \quad (III)$$

in which:

$R_1$, $R_3$, $R_5$, $R_6$, $R_8$ and $R_{10}$ represent a linear or branched, saturated or unsaturated hydrocarbon chain having from 5 to 30 carbon atoms;

$R_2$, $R_4$, $R_7$ and $R_9$ represent a linear or branched, saturated or unsaturated hydrocarbon chain having from 1 to 5 carbon atoms;

the total number of ethylene oxide molecules represented in the above-mentioned formulae I, II and III by k, l+m, n+p+q respectively being an integer such that the HLB value (hydrophilic-lipophilic balance) of said compounds be between about 4 and about 10, preferably between about 5 and about 9.

Generally, the aqueous phase and the self-emulsifiable composition will be mixed in the relative proportions ranging from about 97/3 to about 50/50, preferably 95/5 to about 70/30.

The above-mentioned aqueous phase and the self-emulsifiable composition will each contain from 0 to 100% by weight of the active principle or the active material characterising the product.

The invention will be illustrated in greater detail by the following Examples, given by way of example only, and which consequently will not limit the scope of the invention.

In these examples, the percentages are expressed by weight, unless otherwise indicated.

EXAMPLE 1

Preparation of an Oxyethylenated Methyl Ester of Fatty Acids

Four products were prepared (hereinafter referred to as A, B, C, D) by condensation of ethylene oxide on methyl esters obtained from a fraction derived from fatty acids having 16 and 18 carbon atoms and having the following constitution:

5% Linolenate,
40% Linoleate
32% Oleate,
5% Ricinoleate,
6% Stearate,
6% Palmitate,
QS for 100% Others These ethoxylated methyl esters were prepared according to the following general protocol:

loading the methyl ester in an autoclave;

drying under vacuum at about 120° C.;

adding a basic catalyst such as potassium hydroxide or sodium methoxide;

introducing the amount of ethylene oxide necessary for obtaining the desired molar ratio, under a pressure of 4.5 bars;

maintaining the temperature at about 180° C. for about 45 minutes;

after cooling, neutralising the catalyst with an acid such as formic acid or acetic acid.

The products obtained have the formula I, in which $R_1$ represents a hydrocarbon chain of 15 or 17 carbon atoms which correspond respectively to palmitic, stearic, ricinoleic, oleic, linoleic and linolenic acid residues (by the removal of one hydrogen atom), and $R_2$ represents a methyl radical.

The four products thus obtained were characterised by their saponification index (SI) and their HLB value.

The self-emulsifying power of these products was evaluated by measuring the stability of the emulsions prepared according to the following protocol:

20 g of the ethoxylated ester under study are weighed into a 150 ml beaker, 80 g of town water are then added at ambient temperature and the mixture thus obtained is homogenised with one round of a spatula.

The results obtained are given in Table I below, in which Table is also mentioned the amounts of oil and ethylene oxide by weight which are used to attain the degree of ethoxylated mentioned.

TABLE I

| PRODUCT | A | B | C | D |
|---|---|---|---|---|
| Weight of oil | 100 | 100 | 100 | 100 |
| Weight of ethylene oxide | 15.4 | 31 | 46 | 77 |
| Average degree of ethoxylation (k) | 1 | 2 | 3 | 5 |
| ANALYSIS: | | | | |
| SI | 167 | 147 | 127 | 102 |
| HLB | 3.1 | 5.2 | 7.2 | 9.7 |
| Emulsion stability | <1 H | >4 days | 2 days | A few hrs |

It is noted upon reading this Table that product B containing 2 moles of ethylene oxide is the most efficient.

The HLB value of this product is 5.2.

EXAMPLE 2

Preparation of an Ethoxylated Rapeseed Oil

Five products (hereinafter referred to as E, F, G, H, I) were prepared by condensation of ethylene oxide with rapeseed oil.

The rapeseed oil used in this example originates from French rape and contains fatty chains having from 16 to 22 carbon atoms.

These products were obtained by the following procedure:

loading 2,200 g of rapeseed oil, 44 g of glycerol (2%) and 7 g of a basic catalyst such as potassium hydroxide or sodium methoxide, into an autoclave;

drying under nitrogen bubbling at 100° C. for about 10 minutes;

heating the mixture at 160–180° C., then introducing the amount of ethylene oxide necessary for obtaining the desired molar ratio, under a pressure of 4.5 bars;

maintaining the temperature of the reaction for about 45 minutes;

after cooling, neutralising the catalyst with a weak acid such as formic acid or acetic acid, and filtering.

The presence of glycerol at a relatively low percentage, i. e. lower than about 5% by weight, and preferably in the order of 2% by weight expressed compared to the content of oil to be ethoxylated, facilitates the ethoxylation reaction.

A product of formula III is thus obtained, in which:

$R_6$, $R_8$ and $R_{10}$ represent fatty chains having from 15 to 21 carbon atoms corresponding to the fatty chains of rapeseed oil.

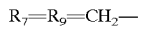

The products obtained were characterised and evaluated in using the same experimental protocols as those mentioned in Example 1, the results obtained are given in Table II below.

TABLE II

| PRODUCT | E | F | G | H | I |
|---|---|---|---|---|---|
| Weight of oil | 2.2 | 2.2 | 2.2 | 2.2 | 2.2 |
| Weight of ethylene oxide | 0.33 | 0.65 | 1.1 | 2.2 | 3.3 |
| average degree of ethoxylation (n + p + q) | 3 | 6 | 10 | 20 | 30 |
| Analysis: SI | 159 | 141 | 120 | 90 | 69 |
| HLB | 2.1 | 4.1 | 6.5 | 9.9 | 12.2 |
| Emulsion stability | <10 min | <10 min | 10 min | 24 H | 10 min |

It is noted that the ethoxylated glycerol triester H (containing 20 moles of ethylene oxide) is the most efficient.

EXAMPLE 3

Preparation of a Self-emulsifiable Composition Containing a Fatty Acid Methyl Ester and a Biodegradable Solvent Product B, described in Example 1 (containing 2 moles of ethylene oxide) has a density of 0.94 and a viscosity of 28 mPas at 25° C.

This product has a good dispersability, i. e. a good aptitude to mix with water without stirring.

It was observed that this dispersability in water can be further improved by mixing this product with an equivalent amount about of a biodegradable solvent, preferably of density greater than 1 to obtain a composition of density neighbouring 1.

Solvents which can be used to this effect are, for example, propylene glycol, glycerine, glycerol triacetate.

Table III below mentions the properties of dispersability and stability of the emulsions obtained according to the same operating method, with product B of Example I and with a 50/50 mixture of this product with glycerol triacetate.

TABLE III

| SELF-EMULSIFIABLE COMPOSITION | PRODUCT B ALONE | PRODUCT B (50%) GLYCEROL TRIACETATE (50%) |
|---|---|---|
| DISPERSIBILITY | GOOD | VERY GOOD |
| EMULSION STABILITY | >4 DAYS | 4 DAYS |

EXAMPLE 4

Preparation of a Self-emulsifiable Composition Containing a Mixture of Ethoxylated Mono- and Tri-ester The ethoxylated glycerol triester H prepared in Example 2 (containing 20 moles of ethylene oxide) has a density of 1.01 and a viscosity of 170 mPas at 25° C.

The density and viscosity characteristics of product B of Example 1 are given in Example 3.

The above-mentioned products B and H were mixed in variable proportions in order to obtain self-emulsifiable compositions of density neighbouring 1 and of low viscosity.

Table IV below summarises the principal characteristics of products B and H, as well as mixtures thereof.

TABLE IV

| Composition | Product B | Product H | PRODUCT B/PRODUCT H MIXTURES | | |
|---|---|---|---|---|---|
| | | | 20/80 | 40/60 | 80/20 |
| Viscosity | 28 mPas | 170 mPas | 113 mPas | 85 mPas | 30 mPas |
| Density | 0.94 | 1.01 | 0.99 | 0.98 | 0.96 |
| Dispersability | Good | Average | Quite good | Good | Good |
| Emulsion stability | >4 days | 1 day | 1 day | 2 days | 4 days |

The mixtures of products B and H, particularly the 80/20 mixture constitute very interesting self-emulsifiable phases.

EXAMPLE 5

Preparation of Self-emulsifiable Compositions Containing Ethoxylated Castor Oils Ethylene oxide is condensed in various proportions with first pressing castor oils.

The synthetic method carried out is similar to that described generally in Example 2, except that it is carried out in the absence of glycerol.

Two products (hereinafter referred to as J and K) were thus prepared.

A composition was also prepared containing product J in a mixture with propylene glycol in the relative proportions 75/25.

The self-emulsifying power of these three products was evaluated according to the protocol described in Example 1, except that the mixture with water was prepared by manual stirring of 6 beats of the 100 ml flask, stoppered beforehand.

The results obtained are mentioned in Table V below.

TABLE V

| PRODUCT | J | K | PRODUCT J 75% PROPYLENE GLYCOL 25% |
|---|---|---|---|
| Weight of oil | 4 | 4 | — |
| Weight of ethylene oxide | 1 | 1.5 | — |
| Average number of moles EO (n + p + q) | 5 | 7 | — |
| SI | 143 | 130 | — |
| HLB | 4.8 | 5.4 | 4.8 |
| Emulsion stability | 3 days | 5 hours | 12 hours |
| Dispersability | Average | Average | Good |

EXAMPLE 6

Preparation of Ethoxylated Methyl Esters of Rapeseed

A methyl ester of rapeseed oil having the following characteristics:
Aspect
  Limpid
Acid index
  0.4
Refractive index at 20° C.
  1.4562
Gardner colour
  3-
Saponification index
  189
Methyl ester content
  96.5%
was ethoxylated with 2, 4, 6 or 8 moles of ethylene oxide.

The synthetic method used was that described in Example 1.

The products thus obtained (referred to as L, M, N and O respectively) correspond to mixtures of products having the general formula I, in which $R_1$ represents a hydrocarbon chain of 15 to 19 carbon atoms corresponding to the fatty chains of rapeseed oil and $R_2$ represents a $CH_3$ group.

These products are emulsified in using the protocol described in Example 1.

Table VI below mentions the properties of the four products synthesised and of their emulsions.

TABLE VI

| PRODUCT | L | M | N | O |
|---|---|---|---|---|
| Weight of oil | 3.7 | 3.7 | 3.7 | 3.7 |
| Weight of ethylene oxide | 1.1 | 2.2 | 3.3 | 4.4 |
| Number EO (k) | 2 | 4 | 6 | 8 |
| SI | 141 | 116 | 89 | 73 |
| HLB | 5.9 | 8.4 | 11.1 | 12.7 |
| Dispersability in water | Very good | Very good | Good | Average |
| Emulsion stability | >2 hours | >2 hours | 2 hours | <15 minutes |

Products L and M (containing 2 and 4 moles of ethylene oxide respectively) prove to be the most efficient.

EXAMPLE 7

Comparison of the Self-emulsifiable Compositions According to the Invention and Commercial Compositions The self-emulsifiable compositions in accordance with the present invention were compared to two commercial oils intended for the preparation of emulsifiable phytosanitary product concentrates.

The characteristics of these commercial oils are the following:

Oil 11E: Alkyl phenol-type surfactant-containing paraffin-type mineral oil having obtained the marketing authorisation No. 6700013 as additive for herbicides;

AGRIROB CM®: Surfactant-containing vegetable oil having obtained the marketing authorisation 8600162 as additive for herbicidal mixture.

These two commercial oils were compared to product B of Example 1, M of Example 6, and H of Example 2.

More specifically, various phytosanitary actives (ETHEPHON®, Chlorpropham®, Formol-lauryl ammonium bromide) were mixed with each one of these products at concentrations used normally.

The dispersion in water of the oils was carried out by following the experimental protocol described in Example 1.

The results obtained are given in Tables VII to X below.

In each case, the stability of the mixture (oil-phytosanitary active), the dispersability, as well as the stability of the aqueous dispersion are measured.

TABLE VII

| | Oils without active | | | | |
|---|---|---|---|---|---|
| Oils | 11E | Agrirob CM® | Product B | Product M | Product H |
| Oil aspect | limpid stable | limpid stable | yellow, stable | yellow, stable | yellow; stable |
| Dispersability | Good | Very good | Good | Good | Quite Good |
| Emulsion stability | #2 H | #2 H | > = 6 H | > = 6 H | <2 H |

TABLE VIII

| Formulations with growth regulator (ETHEPHON) Ethepton 120 g Oil 880 g | | | | | |
|---|---|---|---|---|---|
| Oils | 11E | Agrirob CM® | Product B | Product M | Product H |
| Aspect; formulation stability | Unstable | Unstable | Stable; Limpid | Stable; Limpid | Stable Limpid |
| Dispersability | Average | Average | Very good | Good | Average |
| Emulsion stability 25° | <15 min | <15 min | >24 H | >24 H | <15 min |
| Emulsion stability 40° | Unstable | Unstable | >24 H | >24 H | Unstable |

TABLE IX

| Formulations with herbicide (Chlorpropham) Chlorpropham 450 g Oil 550 g | | | | |
|---|---|---|---|---|
| Oils | 11E | Agrirob CM® | Product B | Product H |
| Aspect; formulation stability | Unstable | Limpid Stable | Limpid Stable | Limpid Stable |
| Dispersability | Average | Average | Average | Average |
| Emulsion stability 25° C. | <15 min | <2 H | <15 min | #24 H |
| Emulsion stability 40° C. | <15 min | Unstable | Unstable | >24 H |

TABLE X

Biocidal formulations
Formol 30% 25 g
Lauryl ammonium bromide 25 g
Oil 950 g

| Oils | 11E | Agrirob CM® | Product B | Product M | Product H |
|---|---|---|---|---|---|
| Aspect; formulation stability | Unstable | Unstable Stable | Limpid Stable 24 H | Hazy Stable | Limpid |
| Dispersability | Average | Average | Good | Good | Average |
| Emulsion stability 25° C. | <15 min | #2 H | >24 H | >24 H | >24 H |
| Emulsion stability 49° C. | <15 min | Unstable | >24 H | >24 H | >24 H |

The results mentioned in the preceding Tables demonstrate that the self-emulsifiable compositions in accordance with the present invention enable obtaining formulations of phytosanitary active principles at least as stable, and often more stable, than the currently commercially available oils.

EXAMPLE 8

Use of the Self-emulsifiable Compositions According to the Invention for Preparing Medicines The use of emulsions is recommended in the pharmaceutical field, especially in the case when a liposoluble active principle is prepared, or even in the case when a slow-release effect is sought after.

The self-emulsifiable oils are particularly useful for extemporaneously preparing emulsions by simple manual stirring or by means of simple devices such as syringes in the case of injectable preparations.

The self-emulsifiable oils usable for such applications must of course be devoid of any toxic effect.

A particular example of pharmaceutical products in which self-emulsifiable oils can be used is that of injectable oily vaccines.

Products B of Example 1 and H of Example 2 have been used for preparing two vaccines containing bovine serum albumin as model antigen.

Doses of 100 μl of vaccines were injected into OF1-type female mice via the sub-cutaneous route.

Each dose contained 50 μg albumin and 25 μl oil.

As control, a preparation containing 50 μg albumin and 25 μl of a commercial oily additive was injected into a third group of mice.

This commercial oily additive is the Montanide® ISA25 product (mineral oil, mannitol oleate).

A fourth group of animals received an aqueous solution of albumin without oil.

The anti-albumin antibody determination (total IgG) is carried out by a conventional ELISA technique 42 days after injection.

The results obtained are given in Table XI below

TABLE XI

| Group | 1 | 2 | 3 | 4 |
|---|---|---|---|---|
| Oil | Product B | Product H | Montanide ISA® | Without Oil |
| Antibody level | 20,000 | 20,000 | 20,000 | 0 |

This Table shows that the two self-emulsifiable oils in accordance with the present invention enable enhancing the immune response at 42 days compared to the control group No. 4 (aqueous solution of albumin without oil).

The extent of this immune response is equivalent to that obtained with the commercial additive.

No intolerance reaction is observed in the animals, nor at the injection sites, nor their general behaviour.

The oils in accordance with the present invention can therefore be used for preparing emulsions which contain a pharmaceutical active principle.

As an example, such an active principle can be an antibiotic, an antigen, an anti-inflammatory, an anti-asthmatic, etc.

What is claimed is:

1. Method of preparing a phytosanitary treatment product or pharmaceutical product in the form of a stable emulsion for veterinary or human use, comprising mixing, without substantial energy input, an aqueous phase, a phytosanitary active material or a medicinal active principle and a self-emulsifiable composition having at least one ethoxylated fatty acid ester of a formula:

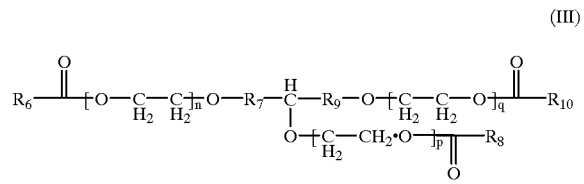

(III)

wherein:

$R_6$, $R_8$ and $R_{10}$ represent a linear or branched, saturated or unsaturated hydrocarbon chain having from 5 to 30 carbon atoms;

$R_7$ and $R_9$ represent a linear or branched, saturated or unsaturated hydrocarbon chain having from 1 to 5 carbon atoms; and n+p+q is an integer such that said at least one ester has an HLB value between about 4 and about 10.

2. Method according to claim 1, wherein said mixing is carried out by slow mechanical stirring.

3. Method according to claim 1, wherein the HLB value is between about 5 and about 9.

4. Self-emulsifiable composition consisting essentially of at least one ethoxylated fatty acid ester having a formula:

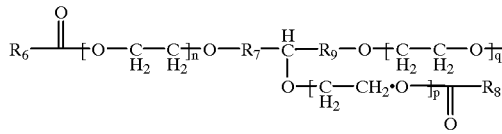

(III)

wherein:

R$_6$, R$_8$ and R$_{10}$ represent a linear or branched, saturated or unsaturated hydrocarbon chain having from 5 to 30 carbon atoms;

R$_7$ and R$_9$ represent a linear or branched, saturated or unsaturated hydrocarbon chain having from 1 to 5 carbon atoms; and n+p+q is an integer such that said at least one ester has an HLB value between about 4 and about 10.

5. Composition according to claim 4, wherein:

R$_6$, R$_8$ and R$_{10}$ represent hydrocarbon chains corresponding to the fatty chains of a vegetable oil;

R$_7$ and R$_9$ represent a methylene group CH$_2$;

n, p and q are integers of sum between 3 and 30.

6. Self-emulsifiable composition consisting essentially of at least one ethoxylated fatty acid ester having a formula:

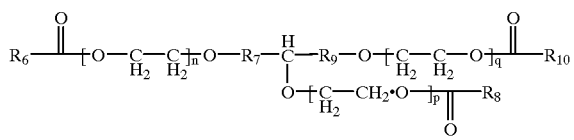

(III)

wherein:

R$_6$, R$_8$ and R$_{10}$ represent hydrocarbon chains corresponding to the fatty chains of rapeseed oil;

R$_7$ and R$_9$ represent a methylene group CH$_2$; and n, p and q are integers of sum between 3 and 30.

7. Self-emulsifiable composition consisting essentially of at least one ethoxylated fatty acid ester having a formula:

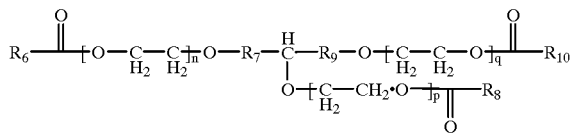

(III)

wherein:

R$_6$, R$_8$ and R$_{10}$ represent hydrocarbon chains corresponding to the fatty chains of castor oil;

R$_7$ and R$_9$ represent a methylene radical CH$_2$; and n, p and q represent integers of sum between 5 and 7.

8. Composition according to claim 6, wherein n, p and q are integers having a sum equal to 20.

9. Phytosanitary treatment product or pharmaceutical product for veterinary or human use, comprising at least one phytosanitary active material or at least one medicinal active principle in association with a self-emulsifiable composition consisting essentially of at least one ethoxylated fatty acid ester of a formula:

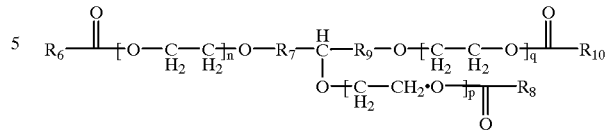

(III)

wherein:

R$_6$, R$_8$ and R$_{10}$ represent hydrocarbon chains corresponding to the fatty chains of a vegetable oil;

R$_7$ and R$_9$ represent a methylene group CH$_2$; and n, p and q are integers of sum between 3 and 30.

10. Phytosanitary treatment product or pharmaceutical product for veterinary or human use, comprising at least one phytosanitary active material or at least one medicinal active principle in association with a self-emulsifiable composition consisting essentially of at least one ethoxylated fatty acid ester of a formula:

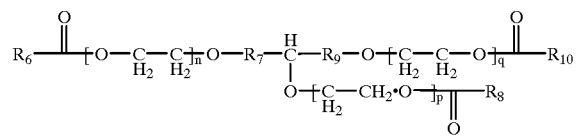

(III)

wherein:

R$_6$, R$_8$ and R$_{10}$ represent hydrocarbon chains corresponding to the fatty chains of rapeseed oil;

R$_7$ and R$_9$ represent a methylene group CH$_2$; and n, p and q are integers of sum between 3 and 30.

11. Composition according to claim 10, wherein n, p and q are integers having a sum equal to 20.

12. Phytosanitary treatment product or pharmaceutical product for veterinary or human use, comprising at least one phytosanitary active material or at least one medicinal active principle in association with a self-emulsifiable composition consisting essentially of at least one ethoxylated fatty acid ester of a formula:

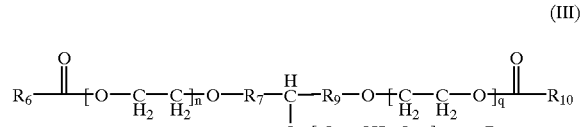

(III)

wherein:

R$_6$, R$_8$ and R$_{10}$ represent hydrocarbon chains corresponding to the fatty chains of castor oil;

R$_7$ and R$_9$ represent a methylene radical CH$_2$; and n, p and q are integers of sum between 5 and 7.

13. Phytosanitary treatment product or pharmaceutical product for veterinary or human use, comprising at least one phytosanitary active material or at least one medicinal active principle in association with a self-emulsifiable composition consisting essentially of at least one ethoxylated fatty acid ester of a formula:

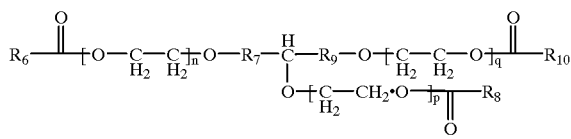

(III)

wherein:

R$_6$, R$_8$ and R$_{10}$ represent a linear or branched, saturated or unsaturated hydrocarbon chain having from 5 to 30 carbon atoms;

R$_7$ and R$_9$ represent a linear or branched, saturated or unsaturated hydrocarbon chain having from 1 to 5 carbon atoms; and n+p+q is an integer such that said at least one ester has an HLB value between about 4 and about 10, said product further comprising a biodegradable solvent which is miscible with said at least one ethoxylated fatty acid ester.

14. Product according to claim 13, wherein said biodegradable solvent is selected from the group consisting of triglycerides, glycols, low molecular weight esters, ketones and mixtures thereof.

15. Product according to claim 13, wherein the self-emulsifiable composition comprises:

50 to 100% by weight of said at least one ethoxylated fatty acid ester; and 0 to 50% by weight of said biodegradable solvent.

16. Phytosanitary treatment product or pharmaceutical product for veterinary or human use, comprising at least one phytosanitary active material or at least one medicinal active principle in association with a self-emulsifiable composition consisting essentially of at least one ethoxylated fatty acid ester of a formula:

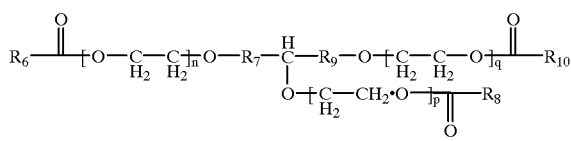

(III)

wherein:

R$_6$, R$_8$ and R$_{10}$ represent a linear or branched, saturated or unsaturated hydrocarbon chain having from 5 to 30 carbon atoms;

R$_7$ and R$_9$ represent a linear or branched, saturated or unsaturated hydrocarbon chain having from 1 to 5 carbon atoms;

n+p+q is an integer such that said at least one ester has an HLB value between about 4 and about 10, wherein said at least one phytosanitary active material or at least one medicinal active principle in association with said self-emulsifiable composition is present in relative proportions ranging from about 1/99 to 90/10.

17. Phytosanitary treatment product or pharmaceutical product for veterinary or human use, comprising at least one phytosanitary active material or at least one medicinal active principle in association with a self-emulsifiable composition consisting essentially of at least one ethoxylated fatty acid ester of a formula:

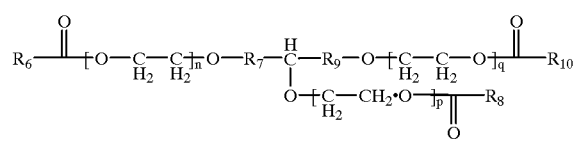

(III)

wherein:

R$_6$, R$_8$ and R$_{10}$ represent a linear or branched, saturated or unsaturated hydrocarbon chain having from 5 to 30 carbon atoms;

R$_7$ and R$_9$ represent a linear or branched, saturated or unsaturated hydrocarbon chain having from 1 to 5 carbon atoms; and n+p+q is an integer such that said at least one ester has an HLB value between about 4 and about 10, said product further comprising an aqueous phase, said product being in the form of a stable emulsion.

18. Composition according to claim 4, wherein the HLB value is between about 5 and about 9.

19. Phytosanitary treatment product or pharmaceutical product for veterinary or human use, comprising at least one phytosanitary active material or at least one medicinal active principle in association with a self-emulsifiable composition consisting essentially of at least one ethoxylated fatty acid ester of a formula:

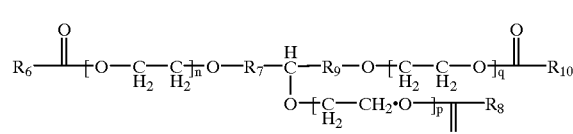

(III)

wherein:

R$_6$, R$_8$ and R$_{10}$ represent a linear or branched, saturated or unsaturated hydrocarbon chain having from 5 to 30 carbon atoms;

R$_7$ and R$_9$ represent a linear or branched, saturated or unsaturated hydrocarbon chain having from 1 to 5 carbon atoms; and n+p+q is an integer such that said at least one ester has an HLB value between about 4 and about 10.

* * * * *